(12) United States Patent
Lau et al.

(10) Patent No.: US 8,377,987 B2
(45) Date of Patent: Feb. 19, 2013

(54) COMPOUNDS AND USES THEREOF FOR TREATING INFLAMMATION AND MODULATING IMMUNE RESPONSES

(75) Inventors: Allan Sy Lau, Hong Kong (CN); Lai Hung Cindy Yang, Hong Kong (CN); Chi Chung Stanley Chik, Hong Kong (CN); Chun Bong James Li, Hong Kong (CN)

(73) Assignees: PuraPharm Company Limited, Hong Kong (CN); Versitech Limited, Hong Kong (CN)

( * ) Notice: Subject to any disclaimer, the term of this patent is extended or adjusted under 35 U.S.C. 154(b) by 398 days.

(21) Appl. No.: 12/647,843

(22) Filed: Dec. 28, 2009

(65) Prior Publication Data
US 2010/0184856 A1 Jul. 22, 2010

Related U.S. Application Data

(60) Provisional application No. 61/143,925, filed on Jan. 12, 2009.

(51) Int. Cl.
*A61K 31/235* (2006.01)
(52) U.S. Cl. ..................................... 514/543
(58) Field of Classification Search ................... 514/543
See application file for complete search history.

(56) References Cited

U.S. PATENT DOCUMENTS 8,017,162 B2 * 9/2011 Shimoda et al. .............. 424/756

FOREIGN PATENT DOCUMENTS

JP 2005-029571 2/2005

OTHER PUBLICATIONS

Mizushina et al (JP2005-029571) English translation 2005.*
Düker et al., "Effects of extracts from *Cimicifuga racemosa* on gonadotropin release in menopausal women and ovariectomized rats," *Planta Med.*, Oct. 1991, pp. 420-424, vol. 57, No. 5, Abstract Only.
Sakurai et al., "[Chemical constituents of original plants of *Cimicifugae rhizoma* in Chinese medicine]," *Yakugaku Zasshi*, Nov. 1996, pp. 850-865, vol. 116, No. 11, Abstract Only.
Burdette et al., "Black Cohosh (*Cimicifuga racemosa* L.) Protects against Menadione-induced DNA Damage through Scavenging of Reactive Oxygen Species: Bioassay-Directed Isolation and Characterization of Active Principles," *Journal of Agricultural and Food Chemistry*, 2002, pp. 7022-7028, vol. 50, No. 24.
Chen et al., "Cimiracemates A-D, phenylpropanoid esters from the rhizomes of *Cimicifuga racemosa*," *Phytochemistry*, 2002, pp. 409-413, vol. 61, No. 4.
Fache et al., "Total synthesis of cimiracemate B and analogs," *Tetrahedron*, 2005, pp. 5261-5266, vol. 61, No. 22.
Grabley, S. et al., "Bioactive agents from natural sources: trends in discovery and application," *Adv Biochem Eng Biotechnol.*, 1999, pp. 101-154, vol. 64.
Habtemariam, S., "Natural inhibitors of tumour necrosis factor-αproduction. Secretion and function," *Planta Med.*, 2000, pp. 303-313, vol. 66.
He et al., *Cimicifuga* species identification by high performance liquid chromatography-photodiode array/mass spectrometric/evaporative light scattering detection for quality control of black cohosh products, *Journal of Chromatography A*, 2006, pp. 241-254, vol. 1112.
Kim et al., "Inhibitory effects of *Cimicifugae rhizoma* extracts on histamine, bradykinin and COX-2 mediated inflammatory actions," *Phytother Res.*, 2000, pp. 596-600, vol. 14.
Kronenberg F. et al., "Complementary and alternative medicine for menopausal symptoms: a review of randomized, controlled trials," *Ann Intern Med.*, 2002, pp. 805-813, vol. 137.
Mizushina et al., "Some anti-chronic inflammatory compounds are DNA polymerase λ-specific inhibitors," *Biochemical Pharmacology*, 2003, pp. 1935-1944, vol. 66, No. 10.
Mizushina et al., "Petasiphenol: a DNA polymerase λ inhibitor," *Biochemistry*, 2002, pp. 14463-14471, vol. 41, No. 49.
Qiu et al., "A triterpene glycoside from black cohosh that inhibits osteoclastogenesis by modulating RANKL and TNFα signaling pathways," *Chem Biol.*, Jul. 2007, pp. 860-869, vol. 14.
Sakai et al., "Inhibitory effect of ferulic acid and isoferulic acid on the production of macrophage inflammatory protein-2 in response to respiratory syncytial virus infection in RAW264.7 cells," *Mediators Inflamm.*, 1999, pp. 173-175, vol. 8.
Takeuchi et al., "Structural relationship of curcumin derivatives binding to the BRCT domain of human DNA polymerase λ," *Genes to Cells*, 2006, pp. 223-235, vol. 11, No. 3.
Tian et al., "*Cimicifuga foetida* extract inhibits proliferation of hepatocellular cells via induction of cell cycle arrest and apoptosis," *J Ethnopharmacol*, 2007, pp. 227-233, vol. 114.

* cited by examiner

*Primary Examiner* — Jennifer M Kim
(74) *Attorney, Agent, or Firm* — Saliwanchik, Lloyd & Eisenschenk

(57) ABSTRACT

The present invention provides compounds, and compositions comprising these compounds, which have immunomodulatory activity and/or anti-inflammatory activity.

11 Claims, 8 Drawing Sheets

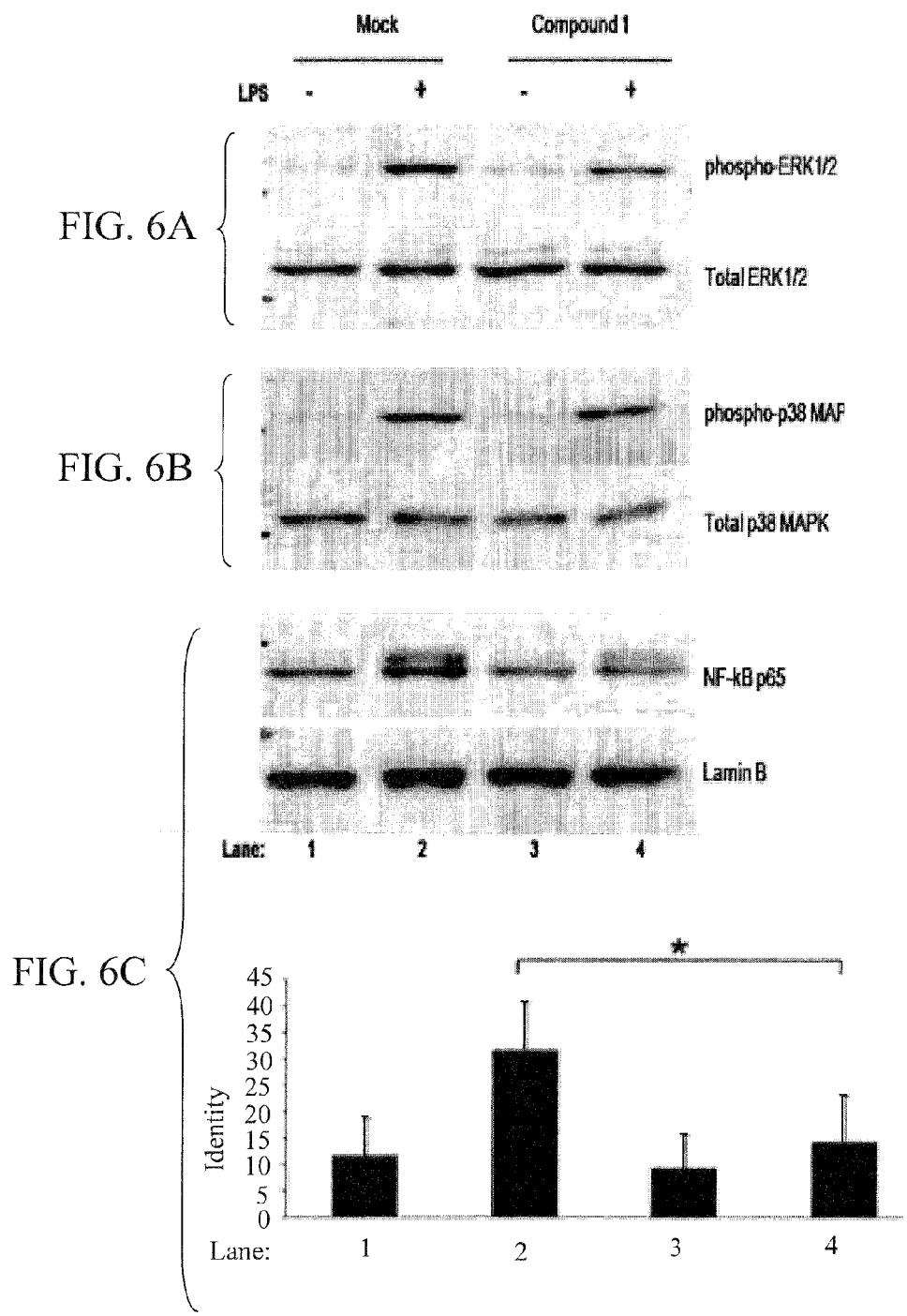

ically available. Common herbs include Ren Shen (*Ginseng*

COMPOUNDS AND USES THEREOF FOR TREATING INFLAMMATION AND MODULATING IMMUNE RESPONSES

CROSS-REFERENCE TO A RELATED APPLICATION

This application claims the benefit of U.S. provisional application Ser. No. 61/143,925, filed Jan. 12, 2009, which is incorporated herein by reference in its entirety, including all figures, tables and sequences.

BACKGROUND OF THE INVENTION

In response to injury, cancer, microbial invasion, and the like, humans mount inflammatory reactions to control the pathological condition and to initiate a repair process. During inflammation, various immune cells including T-lymphocytes, neutrophils and macrophages are recruited to the site of infection and produce cytokines to facilitate the immune response. Among these cytokines, tumor necrosis factor-α (TNF-α) is one of the major proinflammatory proteins to mediate the immune defense.

In addition to acute phase response, TNF-α has been shown to be involved in the progression of various chronic diseases including tumorigenesis and rheumatoid arthritis (RA). The dysregulation of TNF-α production was demonstrated to be involved in different stages of tumorigenesis including initiation of tumor growth[1], cell proliferation[2] and invasion[3]. For tumor cell proliferation, TNF-α upregulates specific growth factors to mediate the malignant growth. The cytokine promotes angiogenesis favoring growth of blood vessels to support the tumor migration, and thus plays a key role in tumor metastasis. For example, glioblastoma migration and induction of metalloproteinases are significantly enhanced in response to TNF-α effects[4].

Examples of chronic disease pathogenesis mediated by TNF-α include rheumatoid arthritis and inflammatory bowel diseases. Patients with rheumatoid arthritis have a low grade insidious inflammation in the synovial tissues. It is known that overproduction of TNF-α at the inflamed joint leads to slow destruction of the joint cartilage and surrounding bone.

During an acute phase of infection such as in the case of sepsis, uncontrolled production of TNF-α is well known to cause deleterious effects to the host. Sepsis is the second most common cause of death in non-coronary intensive care units and the tenth leading cause of death overall in high-income countries[5]. The clinical outcome of infection leading to sepsis is primarily associated with the excessive stimulation of the host immune cells, particularly monocytes or macrophages, by bacterial endotoxins (e.g., lipopolysaccharide [LPS])[6-8]. Macrophages overstimulated by LPS also produce high levels of mediators such as interleukin-1 (IL-1), IL-6, and TNF-α[9]. These mediators are implicated in the pathogenesis of sepsis and found to be contributing factors to the demise of the host. The development of novel therapies directed towards the inhibition of TNF-α production may help to aid in the treatment of these acute and chronic diseases described above.

Following exposure to pathogens and endotoxins, intracellular signaling pathways including specific kinases and transcription factors are activated to induce the expression of TNF-α. The involvement of mitogen-activated protein (MAP) kinases and the nuclear factor kappa B (NF-κB) in pathogen-induced TNF-α expression are well documented[10-12]. *Mycobacteria*, avian influenza and HIV-1 Tat protein are inducers of TNF-α through the MAP kinases[13-15].

There are three MAP kinase subtypes including extracellular signal-regulated kinase-1/2 (ERK 1/2), p38 MAP kinase and c-Jun N-terminal kinase (JNK)[16-20] known in humans. They transduce a variety of extracellular stimuli through a cascade of protein phosphorylations that lead to the activation of transcription factors such as NF-κB. The activation of NF-κB is crucial in production of cytokines including IL-6 and TNF-α[13-15]. The process occurs by the phosphorylation of I-κB at Ser32 and Ser36 via the I-κB kinase (IKK) signalosome complex followed by proteosomal degradation[21] and consequent dissociation of I-κB and NF-κB subunits[22]. The activated NF-κB is then translocated from the cytoplasm to the nucleus, where it binds to κB binding sites in the promoter region of responsive genes, leading to the initiation of transcription of pro-inflammatory mediators. Because inappropriate activation of NF-κB is associated with a wide range of human diseases[23], it has been considered as a plausible target for therapeutic intervention.

Non-steroid anti-inflammatory drugs (NSAIDs) including aspirin, ibuprofen, and indomethacin are well-known in ameliorating acute and chronic pain associated with inflammatory diseases such as rheumatoid arthritis and inflammatory bowel disease. However, they are not effective in the treatment of advanced stages of rheumatoid arthritis and related autoimmune diseases. For those conditions, steroids and cytotoxic drugs such as methotrexate and cyclophosphamide are used. These drugs are associated with severe adverse effects including gastrointestinal irritation, severe bleeding, and bone marrow suppression.

In recent years, immunotherapeutics have been developed which aim at the neutralization of TNF-α and suppression of its undesirable proinflammatory effects. These include soluble TNF-α receptor (Enbrel) and anti-TNF-α antibody (Infliximab). Despite their novelty and efficacy in the arrest of disease progression, they are very expensive therapeutic regimens.

Considerable effort has been made in efforts to discover bioactive agents from natural sources, especially from microbes, plants, and marine organisms. Plants act as an alternative and supplemental source of new medicine, as they contain a variety of previously unknown chemicals that may have potent biological effects.

Traditional Chinese medicine has been practiced by the Chinese people for 2-3 millennia. It deals with pathology, and diagnosis, treatment and prevention of diseases. Chinese medicinal materials have been recorded in various pharmacopoeia. One of the classical references for medicinal herbs is *Ben Cao Gang Mu* written by Li Shizhen in the late 14$^{th}$ Century. The book contains about 2,500 items of herbs and other products including animals and minerals.

Herbs used in traditional Chinese medicine are commercially available. Common herbs include Ren Shen (*Ginseng* radix), Gang Gui (*Angelica sinensis* radix), Huang Qi (*Astragali* radix), Gan Cao (the rhizome of *glycyrrhiza uralensis* Fisch., *Glycyrrhiza glabra* L. or *Glycyrrhiza inflata* Bat, and preferably *Glycyrrhiza uralensis* Fisch), and Huang Qin (*Scutellariae* radix). Commonly, herbs are obtained in their dry forms, sometimes already grinded into powder.

*Cimicifuga rhizome* has a long and diverse history of medicinal use in the Eastern United States and Canada[26]. Historically, native American Indians used it to treat a variety of conditions including malaise, malaria, rheumatism, abnormalities in kidney function, sore throat, menstrual irregularities, and menopause[26-28]. In Asian countries including China, Japan and Korea, *Cimicifuga racemosa* and its counterparts *Cimicifuga heracleifolia, Cimicifuga foetida* and *Cimicifuga* dahurica have been used as traditional medicinal herbs to treat fever, pain and inflammation[29-30].

Previous studies demonstrated the inhibitory effects of *Cimicifuga racemosa* extract on histamine, bradykinin and cyclooxygenase-2 (COX-2) mediated inflammatory actions[31]. The extract also has protective effects against menadione-induced DNA damage through its scavenging effects on reactive oxygen species[32]. In addition, *Cimicifuga heracleifolia* extracts has been demonstrated to have antiviral activities against respiratory syncytial virus[30]. In a recent study, *Cimicifuga foetida* extracts were shown to induce apoptosis and cell cycle arrest of hepatocarcinoma cells, which are critical effects in inhibiting the tumor progression[33]. Also, the actions of *Cimicifuga racemosa* on menopause-regulated response have been well studied[36]. These data indicate that the constituents of *Cimicifuga racemosa* might function similar to that of estrogen. Other studies showed that *Cimicifuga racemosa* perturbs cytokine signaling in order to mediate other biological functions[37].

Currently, in the treatment for rheumatoid arthritis, psoriasis, psoriatic arthritis and ankylosing spondylitis, monoclonal TNF-α antibody plays an important role in the control of disease progression. Similarly, several randomized, double blind, placebo-controlled clinical trials had been performed in patients with Crohn's disease. The results of these clinical trials showed that the anti-TNF-α antibody (Infliximab) has beneficial effects to the patients[41].

Additionally, recent studies showed that inflammatory responses including TNF-α production may play an important role in the pathogenesis of cardiovascular diseases (CVD). It has been suggested that TNF-α may destabilize the atherogenesis and atherosclerotic plaques leading to their rupture, resulting in myocardial infraction or stroke in CVD patients.

During microbial infection, macrophages are activated to produce cytokines to mediate immune response. Depending on the invading microbe and its biological properties, the host immune system utilizes different sets of cytokines to combat the invading pathogen locally and systemically.

A good example is mycobacterial infection, in which the proinflammatory cytokines TNF-α plays a critical role in host survival by propagating inflammation to contain the microbes by the formation of granuloma[42]. The protective role of TNF-α in controlling mycobacterial growth is exemplified by the resurgence of tuberculosis in patients receiving anti-TNF-α antibody therapy[43].

Although the effects of proinflammatory cytokines are protective, their overproduction may have adverse effects to the host. In fact, uncontrolled induction of proinflammatory cytokine can lead to complications such as hypotension, organ failure and even death[44,45]. Indeed, the overproduction of TNF-α in endotoxemia patients leads to serious deleterious symptoms. In chronic diseases such as rheumatoid arthritis, TNF-α overexpression is known to be the damaging factor and is associated with progressive joint destruction[46].

BRIEF SUMMARY

The present invention provides compounds, and compositions comprising these compounds, which have immunomodulatory activity and/or anti-inflammatory activity. In certain embodiments, because of the effects of these compounds on TNF-α, they have immunomodulatory activity that is not specifically associated with inflammation.

One embodiment of the subject invention pertains to a compound isolated from herbs. Advantageously, this compound possesses potent anti-inflammatory and immunomodulatory effects.

The present invention thus relates to a substantially pure anti-inflammatory compound having the following structure:

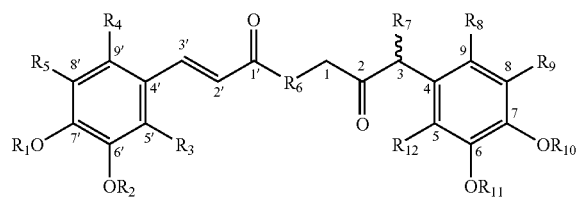

wherein $R_1$ is alkyl;

$R_2$ is H or alkyl;

$R_3$, $R_4$, and $R_5$ are independently —H, acyl, halo, haloalkyl, amino, alkylamino, hydroxyl, alkyl, hydroxylalkyl, or —COOH;

$R_6$ is —O or —NH;

$R_7$ is —H, alkyl, alkoxy, hydroxylalkyl, hydroxyl, or halo;

$R_8$, $R_9$, and $R_{12}$ are independently —H, acyl, halo, amino, alkylamino, hydroxyl, alkyl, hydroxylalkyl, or —COOH;

$R_{10}$ is H or alkyl; and $R_{11}$ is H or alkyl;

Advantageously, in one embodiment, the compounds of the subject invention can inhibit LPS-induced TNF-α production. (AL-to-David please consider adding this with IP language: Due to its potent inhibition of endotoxin (LPS) effects, the use of the compounds of the subject compounds of the subject invention can be applied beyond endotoxemia to include inflammatory conditions found in autoimmune diseases and other related conditions.

The present invention is also directed to pharmaceutical compositions comprising a pharmaceutically acceptable carrier and an anti-inflammatory compound of the invention. In a preferred embodiment, the composition contains the anti-inflammatory compound as the active ingredient.

The present invention is also directed to methods of use of the compounds or compositions comprising them, for the inhibition of inflammation in animals, preferably mammals, including humans. The present invention is also directed to methods of use of said compounds or compositions comprising said compounds for the modulation of immune activity in animals, preferably mammals, including humans.

BRIEF DESCRIPTION OF THE DRAWINGS

FIGS. 6A-6C show the effects of B22EES1-8-3 on LPS-induced phosphorylation (phospho-) of ERK1/2 and p38 MAP kinases, and nuclear translocation of NF-κB p65. PBMac were incubated with B22EES1-8-3 (140 μM) for 24 h prior to the addition of 10 ng/mL LPS for an additional 15 min. Cytoplasmic (A, B) and nuclear (C) proteins were harvested for Western Blotting: (A) Cytoplasmic proteins: phospho-ERK1/2 and total ERK1/2. (B) Cytoplasmic proteins: phospho-p38 and total p38 kinase. (C) Nuclear proteins: upper panel, NF-κB p65 and lamin B; lower panel, the intensity of corresponding lanes in the gel photograph of NF-κB p65 was shown. The results shown are representative of at least three independent experiments, with cells obtained from different donors. *P<0.05, compared with the corresponding control.

BRIEF DESCRIPTION OF THE SEQUENCES

Figure 1:
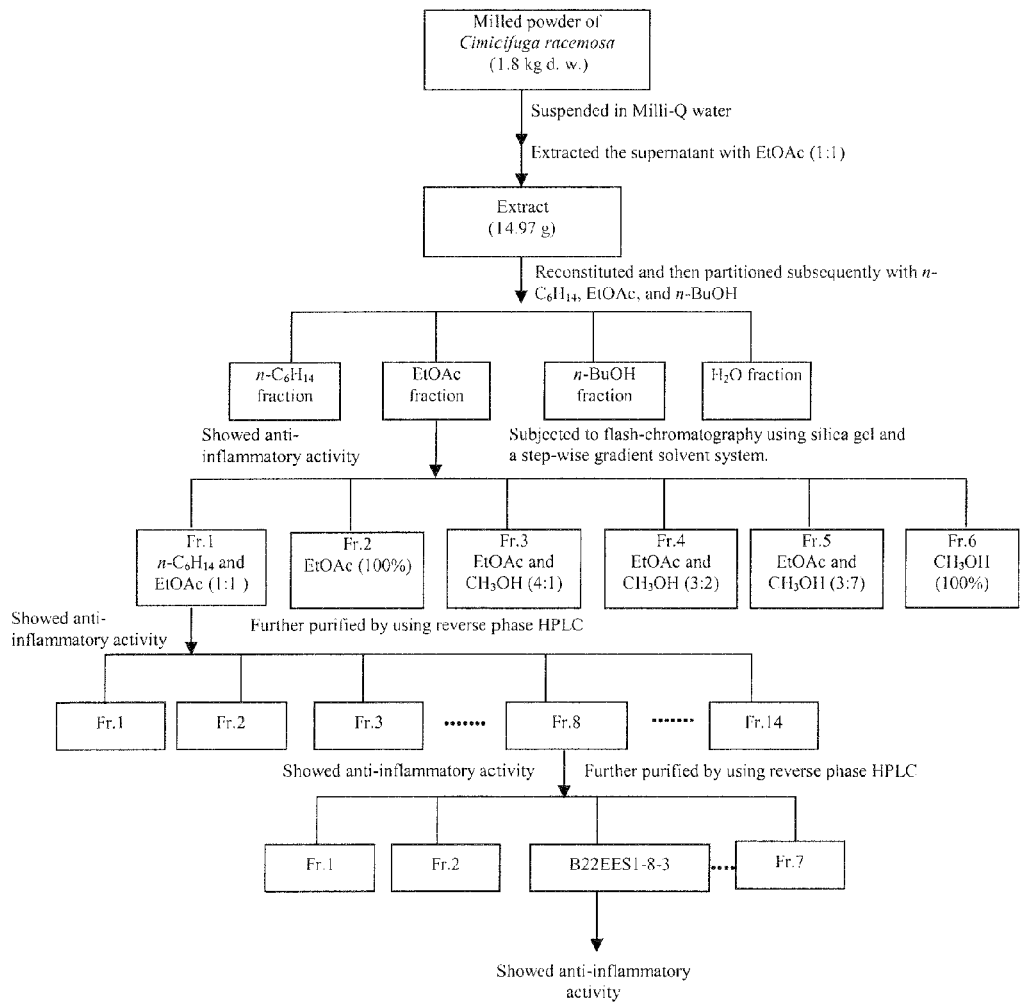
FIG. 1 shows an extraction scheme of B22EES1-8-3 from *Cimicifuga racemosa*. *Cimicifuga racemosa* (1.8 kg) was milled and extracted with 500 mL milli-Q water for 1 hr with continuous sonication. The collected supernatant was then partitioned with ethyl acetate (EtOAc) (1:1). The resulting dried EtOAc extract was reconstituted and then sequentially partitioned with hexane (n-$C_6H_{14}$), EtOAc and butanol (n-BuOH). Using bioassay guided fractionation scheme, the fractions showing inhibitory effects on LPS-induced TNF-α production were subjected to silica gel 60A (35-75 μm) chromatography and reversed-phase high-performance liquid chromatography using gradient elution until a single compound with anti-inflammatory activity was obtained.

SEQ ID NO:1 is a primer useful according to the subject invention.

SEQ ID NO:2 is a primer useful according to the subject invention.

SEQ ID NO:3 is a primer useful according to the subject invention.

SEQ ID NO:4 is a primer useful according to the subject invention.

DETAILED DESCRIPTION

Novel and advantageous compounds have been identified according to the subject invention. Advantageously, these molecules have useful immunomodulatory and/or anti-inflammatory properties. The present invention further provides compositions comprising these compounds as well as methods for the use in treating inflammatory and immune conditions in a subject.

One embodiment of the subject invention pertains to a compound isolated from herbs. Advantageously, this compound possesses potent anti-inflammatory and immunomodulatory effects.

The present invention thus relates to a substantially pure anti-inflammatory compound having the following structure:

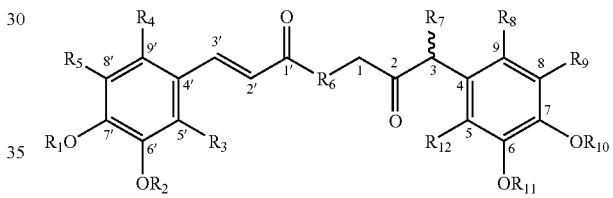

wherein
Wherein
R$_1$ is alkyl;
R$_2$ is H or alkyl;
R$_3$, R$_4$, and R$_5$ are independently —H, acyl, halo, haloalkyl, amino, alkylamino, hydroxyl, alkyl, hydroxylalkyl, or —COOH;
R$_6$ is —O or —NH;
R$_7$ is —H, alkyl, alkoxy, hydroxylalkyl, hydroxyl, or halo;
R$_8$, R$_9$, and R$_{12}$ are independently —H, acyl, halo, amino, alkylamino, hydroxyl, alkyl, hydroxylalkyl, or —COOH;
R$_{10}$ is H or alkyl; and
R$_{11}$ is H or alkyl;

"Alkyl" means linear saturated monovalent radicals of one to eight carbon atoms or a branched saturated monovalent of three to eight carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

"Acyl" means a radical —C(O)R where R is hydrogen, alkyl or cycloalkyl, or heterocycloalkyl. Examples include formyl, acetyl, ethylcarbonyl, and the like.

"Halo" means fluoro, chloro, bromo, or iodo, such as bromo and chloro.

"Haloalkyl" means alkyl substituted with one or more same or different halo atoms, e.g., —CH$_2$Cl, —CH$_2$Br, —CF$_3$, —CH$_2$CH$_2$Cl, —CH$_2$CCl$_3$, and the like.

An "amino" is intended to mean the radical —NH$_2$.

"Alkylamino" means means a radical —NHR or —NR$_2$ where each R is independently an alkyl group. Examples include methylamino, (1-methylethyl)amino, methylamino, dimethylamino, methylethylamino, di(1-methyethyl)amino, and the like.

A "hydroxy" is intended to mean the radical —OH.

Hydroxyalkyl" means an alkyl radical as defined herein, substituted with one or more, preferably one, two or three hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl and 1-(hydroxymethyl)2-hydroxyethyl.

An "alkoxy" is intended to mean the radical —OR$_a$, where R$_a$ is an alkyl group. Exemplary alkoxy groups include methoxy, ethoxy, propoxy, and the like.

The subject invention further pertains to isolated enantiomeric compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

In a specific embodiment, the subject invention pertains to a compound referred to herein as B22EES1-8-3 (abbreviated as B8-3), which was identified after 5 rounds of extraction. The structure of B8-3 is:

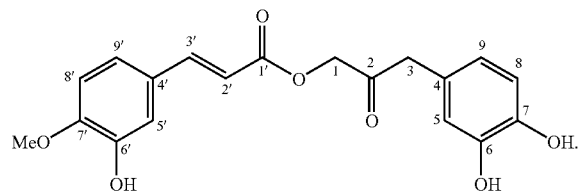 [SMILES: COc1ccc(/C=C/C(=O)OCC(=O)Cc2ccc(O)c(O)c2)cc1O]

Advantageously, this compound inhibits TNF-α induction.

After the identification of B8-3, its biological activities were compared to dexamethasone, the standard drug for immunosuppression. Incubation with B8-3 ameliorated the LPS-upregulated TNF-α production by over 50% (FIG. 5A), which is comparable to the effects of dexamethasone (FIG. 5B).

Dexamethasone is an effective drug used in the treatment of many autoimmune diseases. Unfortunately, the use of dexamethasone is well known to have side effects to the patients. Since B8-3 is isolated from the herbs including *Cimicifuga foetida* and *Cimicifuga heracleifolia*, the toxicity of the herbs in human uses has been well tested for centuries.

Furthermore, it was determined that the activation of MAP kinase and NF-κB can be abrogated by B8-3. These two mediators play a key role in cytokine production and, thus, regulating multiple immune responses. B8-3 can also be used according to the subject invention to regulate the downstream effectors of TNF-α.

B8-3 was isolated from *Cimicifuga racemosa* and its Chinese counterparts using unique isolation and bioassay-guided procedures. The effects of B8-3 on the regulation of cytokines occur via its activity in the modulation of signaling kinase and transcription factor activities. B8-3 suppresses mitogen induced inflammatory response, which makes this molecule useful for treatment of a variety of clinical conditions. Since overproduction of TNF-α is toxic and can result in severe complications, limiting the overwhelming inflammatory response can be beneficial to patients in clinical management. This is the first study to identify an active anti-inflammatory compound in *Cimicifuga racemosa* and its Chinese counterparts. The compounds of the subject invention can also be used to treat inflammation associated with infection, including, but not limited to, infections by viruses, bacteria, fungi, yeast, and other microbes. Additionally, the compounds of the subject invention can be used to treat inflammation mediated by a variety of factors including, but not limited to, interferons, interleukins, and environmental toxins.

The compounds and pharmaceutical compositions of the present invention can be used in the treatment, or amelioration, of inflammatory symptoms in any disease, condition or disorder where immune and/or inflammation suppression is beneficial. Inflammatory diseases, conditions or disorders in which the compounds and compositions of the present invention can be used to inhibit unwanted immune reactions and inflammation include, but are not limited to, arthritis, including but not limited to rheumatoid arthritis, and other diseases, conditions or disorders of the joints or musculoskeletal system in which immune and/or inflammation suppression is beneficial.

Moreover, the compounds and compositions are also useful to treat or ameliorate inflammation associated with atherosclerosis; arteriosclerosis; atherosclerotic heart disease; reperfusion injury; cardiac arrest; myocardial infarction; vascular inflammatory disorders including cerebro-vascular disease (stroke); respiratory distress syndrome and other cardiopulmonary diseases, conditions or disorders where immune and/or inflammation suppression would be beneficial.

In addition, the compounds and compositions are also useful to treat or ameliorate inflammation associated with peptic ulcer; ulcerative colitis, Crohn's Disease, irritable bowel syndrome, other inflammatory bowel conditions, and other diseases, conditions or disorders of the gastrointestinal tract where immune inflammation suppression would be beneficial; hepatic fibrosis; liver cirrhosis and other hepatic diseases, conditions or disorders where immune and/or inflammation suppression would be beneficial; thyroiditis and other glandular diseases, conditions or disorders where immune and/or inflammation suppression would be beneficial; glomerulonephritis and other renal and urologic diseases, conditions or disorders where immune and/or inflammation suppression would be beneficial.

In addition, the compounds and compositions are also useful to treat or ameliorate inflammation associated with post-traumatic inflammation; septic shock; infectious diseases where immune and/or inflammation suppression would be beneficial; inflammatory complications and side effects of surgery where immune and/or inflammation suppression would be beneficial; bone marrow transplantation and other transplantation complications and/or side effects where immune and/or inflammation suppression would be beneficial; inflammatory and/or immune complications and side effects of gene therapy, e.g., due to infection with a viral carrier; and inflammation associated with acquired immune deficiency syndrome (AIDS).

Further, the compounds and compositions are also useful to inhibit macrophage or T cell associated aspects of an immune response that are not associated with inflammation. The compounds and compositions are able to inhibit macrophage or T cell activities including, but not limited to, macrophage antigen-presenting activity, macrophage cytokine production, T cell cytokine production, T cell adhesion activity, T cell proliferation, etc. Thus, the peptides, peptide derivatives and compositions are useful to suppress or inhibit a humoral and/or cellular immune response.

The compounds and compositions are also useful to treat or ameliorate monocyte and leukocyte proliferative diseases, e.g., leukemia, by reducing the amount of monocytes and lymphocytes.

The compounds and pharmaceutical compositions of the invention are further useful for the prevention and/or treatment of graft rejection in cases of transplantation of natural or artificial cells, tissue and organs, such as cornea, bone marrow, organs, lenses, pacemakers, natural and artificial skin tissue, and the like.

The compounds and compositions are also useful to treat or ameliorate inflammation associated with hypersensitivity; allergic reactions; asthma; systemic lupus erythematosus; collagen diseases and other autoimmune diseases, conditions or disorders in which immune and/or inflammation suppression is beneficial.

The compounds and compositions are also useful to treat or ameliorate inflammation associated with otitis and other otorhinolaryngological diseases, conditions or disorders where immune and/or inflammation suppression would be beneficial; dermatitis and other dermal diseases, conditions or disorders where immune and/or inflammation suppression would be beneficial; periodontal diseases and other dental diseases, conditions or disorders where immune and/or inflammation suppression would be beneficial.

In addition, the compounds and compositions are also useful to treat or ameliorate inflammation associated with posterior uveitis; intermediate uveitis; anterior uveitis; conjunctivitis; chorioretinitis; uveoretinitis; optic neuritis; intraocular inflammation, such as retinitis and cystoid macular edema; sympathetic ophthalmia; scleritis; retinitis pigmentosa; immune and inflammatory components of degenerative fondus disease; inflammatory components of ocular trauma; ocular inflammation caused by infection; proliferative vitreoretinopathies; acute ischemic optic neuropathy; excessive scarring, for example, following glaucoma filtration operation; immune and/or inflammation reaction against ocular implants and other immune and inflammatory-related ophthalmic diseases, conditions or disorders where immune and/or inflammation suppression would be beneficial.

Moreover, the compounds and compositions are also useful to treat or ameliorate inflammation associated with autoimmune diseases and conditions or disorders where, both in the central nervous system (CNS) and in any other organ, immune and/or inflammation suppression would be beneficial; Parkinson's disease; complications and/or side effects from treatment of Parkinson's disease; AIDS-related dementia complex (HIV-related encephalopathy); Devic's disease; Sydenham chorea; Alzheimer's disease and other degenerative diseases, conditions or disorders of the central nervous system where immune and/or inflammation suppression would be beneficial; inflammatory components of strokes; post-polio syndrome; immune and inflammatory components of psychiatric disorders; myelitis; encephalitis; subacute sclerosing panencephalitis; encephalomyelitis; acute neuropathy; subacute neuropathy; chronic neuropathy; Guillaim-Barre syndrome; Sydenham chorea; myasthenia gravis; pseudotumor cerebri; Down's Syndrome; Huntington's disease; amyotrophic lateral sclerosis; inflammatory components of central nervous system (CNS) compression or CNS trauma or cerebrovascular accidents (stroke) or infections or hypoxia-ischemia of the CNS; inflammatory components of muscular atrophies and dystrophies; and immune and inflammatory related diseases, conditions or disorders of the central and peripheral nervous systems where immune and/or inflammation suppression would be beneficial.

In yet another embodiment, the compounds and compositions of the invention are useful to restore immune privilege at an immune privileged site which has lost its immune privilege such as brain, eye and testis.

In one embodiment, the subject invention provides isolated compounds. As used herein, "isolated" refers to compounds that have been removed from any environment in which they may exist in nature. For example, isolated B8-3 would not refer to the B8-3 compound as it exists in *C. racemosa*. In preferred embodiments, the compounds of the subject invention are at least 75% pure, preferably at least 90% pure, more preferably are more than 95% pure, and most preferably are more than 99% pure (substantially pure).

The present invention also provides for therapeutic or pharmaceutical compositions comprising a compound of the invention in a form that can be combined with a pharmaceutically acceptable carrier. In this context, the compound may be, for example, isolated or substantially pure. The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier. As used herein carriers do not include the natural plant material as it exists in nature.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In one embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The present invention also provides for the modification of the compound such that it is more stable once administered to a subject, i.e., once administered it has a longer time period of effectiveness as compared to the unmodified compound. Such modifications are well known to those of skill in the art, e.g., polyethylene glycol derivatization (PEGylation), microencapsulation, etc.

The amount of the therapeutic or pharmaceutical composition of the invention which is effective in the treatment of a particular disease, condition or disorder will depend on the nature of the disease, condition or disorder and can be determined by standard clinical techniques. In general, the dosage ranges from about 0.001 mg/kg to about 2 mg/kg. In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. For example, in order to obtain an effective mg/kg dose for humans based on data generated from rat studies, the effective mg/kg dosage in rats is divided by six.

The invention also provides a pharmaceutical pack or kit comprising one or more containers filled with one or more of the ingredients, e.g., compound, carrier, of the pharmaceutical compositions of the invention.

The compounds of the subject invention can also be formulated consistent with traditional Chinese medicine practices. The composition and dosage of the formulation that are effective in the treatment of a particular disease, condition or disorder will depend on the nature of the disease, condition or disorder by standard clinical techniques.

The traditional Chinese medicine in prescription amounts can be readily made into any form of drug, suitable for administering to humans or animals. Suitable forms include, for example, tinctures, decoctions, and dry extracts. These can be taken orally, applied through venous injection or mucous membranes. The active ingredient can also be formulated into capsules, powder, pallets, pastille, suppositories, oral solutions, pasteurized gastroenteric suspension injections, small or large amounts of injection, frozen power injections, pasteurized powder injections and the like. All of the above-mentioned methods are known to people skilled in the art, described in books and commonly used by practitioners of herbal medicine.

A tincture is prepared by suspending herbs in a solution of alcohol, such as, for example, wine or liquor. After a period of suspension, the liquid (the alcohol solution) may been administered for example, two or three times a day, one teaspoon each time.

A decoction is a common form of herbal preparation. It is traditionally prepared in a clay pot, but can also be prepared in glass, enamel or stainless steel containers. The formulation can be soaked for a period of time in water and then brought to a boil and simmered until the amount of water is reduced by, for example, half.

An extract is a concentrated preparation of the essential constituents of a medicinal herb. Typically, the essential constituents are extracted from the herbs by suspending the herbs in an appropriate choice of solvent, typically, water, ethanol/water mixture, methanol, butanol, iso-butanol, acetone, hexane, petroleum ether or other organic solvents. The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract, extracum siccum, by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

Materials and Methods
Plant Material

*Cimicifuga racemosa* was purchased from the Glenbrook Farms Herbs and Such, Campbellsville, Ky. *Cimicifuga heracleifolia, Cimicifuga foetida* and *Cimicifuga dahurica* were purchased in herbal markets and subsequently authenticated by Purapharm with respect to their identification.

Extraction and Isolation of the Bioactive Molecules

The procedures for plant extraction are shown in FIG. 1. Briefly, *Cimicifuga racemosa* (1.8 kg) was milled, homogenized and then suspended in (1:5) milli-Q water for 1 hr with continuous sonication. The supernatant was filtered through an analytical filter paper and then partitioned three times with ethyl acetate (EtOAc) (1:1). The resulting EtOAc extract was concentrated to dryness in vacuo (35° C.) to yield 14.97 g of a dark brown residue. The residue was reconstituted in methanol (MeOH) and then fractionated by partitioning with hexane (n-$C_6H_{14}$). The MeOH fraction was concentrated and reconstituted in $H_2O$ and then partitioned sequentially with EtOAc and butanol (n-BuOH). Four fractions, namely n-$C_6H_{14}$, EtOAc, n-BuOH, and $H_2O$ were obtained.

The fraction that showed inhibitory effects on LPS-induced TNF-α production was subjected to additional silica gel 60A (35-75 μm) chromatography using n-$C_6H_{14}$, EtOAc, and MeOH to yield six fractions. The active fractions were further purified by reversed-phase high-performance liquid chromatography (HPLC) (Lichrospher 100 RP C18 EC 5μ, 250×4.6 mm ID) using a gradient elution from 25% acetonitrile ($CH_3CN$) to 90% $CH_3CN$ at a flow rate of 1 mL min$^{-1}$.

Peak detection was achieved using an Agilent 1200 series of fast scanning Photo-diode Array detector set at 254, 210 and 280 nm. Eluting peaks were scanned between 200 nm and 300 nm with 1 nm intervals to determine absorbance maxima and minima.

By repeating the purification process using HPLC, a single compound was eluted at approximately 9.4 minutes with UV absorbance maximized at 290 and 325 nm, which revealed that it has a conjugated aromatic system. This compound (B22EES1-8-3) showed anti-inflammatory activities.

Elucidation of the Molecular Structure

The structure of the resulting pure compound (B22EES1-8-3) was elucidated by using a Bruker 500 MHz DRX NMR spectrometer, operating at 500 MHz for $^1$H and at 125.765 MHz for $^{13}$C NMR, using methanol-d as the solvent. Distortionless enhancement by polarization transfer (DEPT) experiments were performed using a transfer pulse of 135° to obtain positive signals for CH and $CH_3$, and negative signals for $CH_2$. HR-ESI-MS was performed on a micrOTOF II 411 ESI-TOF mass spectrometer (Bruker Daltonics). Data sets were acquired in negative electrospray (ESI) mode in a scan ranging from 100 to 1600 m/z at a sampling rate of 2 Hz. ESI parameters were as follows: capillary, 3.2 kV; nebulizer pressure, 4 bar; dry 415 gas flow, 8 L/min; and dry gas temperature, 200° C.

The 13C NMR spectra of the compound showed signals at δ 68.6 (t, C-1), 204.6 (s, C-2), 46.4 (t, C-3), 126.1 (s, C-4), 117.7 (d, C-5), 146.7 (s, C-6), 145.8 (s, C-7), 116.7 (d, C-8), 122.1 (d, C-9), 168.3 (s, C-1'), 115.3 (d, C-2'), 147.6 (d, C-3'), 128.9 (s, C-4'), 114.9 (d, C-5'), 148.2 (s, C-6'), 151.8 (s, C-7'), 112.6 (d, C-8'), 123.1 (d, C-9'), and 56.5 (q, MeO-7'). In addition, the compound showed a [M]-ion peak at m/z 357.0952 in its HR-ESI-MS, consistent with the molecular formula $C_{19}H_{17}O_7$ (calc. 357.0974).

Determination of the Presence of B22EES1-8-3 in *C. foetida* and *C. heracleifolia* Using HPLC-UV and HPLC-TOF-MS Herbs *C. foetida* and *C. heracleifolia* were extracted following the extraction procedure of *C. racemosa* as described above. The extracts of Herbs *C. foetida* and *C. heracleifolia* (CF22EES1-8 and CH22EES1-8) were injected into the HPLC equipped with a PDA detector following the chromatographic conditions that were used to isolate B22EES1-8-3. The chromatogram of individual sample was recorded. CF22EES1-8 and CH22EES1-8 were also injected separately into an Acquity UPLC system (Waters, USA) equipped with an Xterra MSC18 column (150*2.1 mmID, 3.5522 μm). Chromatographic separations were performed using a gradient elution from 25% acetonitrile ($CH_3CN$) to 90% $CH_3CN$ at a flow rate of 200 μL/min. Eluted compounds were detected using a micrOTOF II ESI-TOF mass spectrometer (Bruker Daltonics). Data sets were acquired in negative electro spray (ESI) mode in a scan ranging from 100 to 1600 m/z at a sampling rate of 2 Hz. ESI parameters were as follows: capillary, 3.2 kV; nebulizer pressure, 4 bar; dry gas flow, 8 L/min; and dry gas temperature, 200° C.

By comparing their peaks with the standard of B22EES1-8-3, the presence of B22EES1-8-3 in the extract of *C. foetida* and *C. heracleifolia* were determined.

Chemicals

Endotoxin (lipopolysacharride, LPS) from *E. coli* was purchased from Sigma and used as an inducer of TNF-α expression. Dexamethasone (Sigma) was used as a control drug to inhibit the LPS induction of TNF-α.

Cell Culture and Primary Blood Macrophage Isolation

Human peripheral blood monocytic cells (PBMC) were isolated from the buffy coat of healthy donor blood supplied by Hong Kong Red Cross by Ficoll-Paque (Amersham Pharmacia Biotech, Piscataway, N.J.) density gradient centrifugation as described in our previous reports[14,15,34]. In brief, the buffy coat was spun at 3000 rotations per min (rpm) for 15 min to separate the blood cells and the plasma. The heat inactivated serum was filtered for future use.

The cell layer was diluted with phosphate buffered saline (PBS) in a ratio of 1:1. The diluted cells were overlaid on Ficoll-Paque slowly and centrifuged at 2300 rpm for 20 min for separation of mononuclear cells from erythrocytes. The mononuclear cell layer was removed and washed with RPMI 1640 medium until the supernatant was clear.

The cells were finally resuspended in RPMI 1640 medium supplemented with 5% autologous serum and cultured for 1 hr. The non-adherent cells were removed afterwards and the remaining adherent cells were further incubated for another 24 hr at 37° C. in 5% carbon dioxide ($CO_2$).

The adherent monocytic cells were detached and seeded onto tissue culture plates and incubated for another 7-14 days in order to differentiate the primary blood monocytic cells to primary blood macrophages (PBMac).

Isolation of RNA and Reverse Transcription

Total RNA from primary blood macrophages with or without treatment of *Cimicifuga racemosa* fractions was extracted by TRIzol (Invitrogen). Reverse transcription (RT) of messenger RNA (mRNA) to complementary DNA (cDNA) was done by using the SuperScript II system (Invitrogen) as per the manufacturer's instruction.

Polymerase Chain Reaction (PCR) and Real-Time RT-PCR

Semi-quantitative PCR assays of targeted genes were performed in a 25 μl reaction mixture containing 1.5 mM $MgCl_2$, 0.2 mM of each deoxynucleoside triphosphate, 0.25 μM of each primer, 2 units of Taq polymerase (Amersham Pharmacia Biotech, Piscataway, N.J.), and 1 μl of cDNA. PCR primer sets for TNF-α and glyceraldehyde-3-phosphate dehydrogenase (GAPDH) were as follows. TNF-α (upstream: 5'-GGCTCCAGGCGGTGCT TGTCC-3' (SEQ ID NO:1); downstream: 5'-AGACGGCGATGCGGCTGATG-3' (SEQ ID NO:2)), and GAPDH (upstream: 5'-ACCACAGTCCAT-GCCATCAC-3' (SEQ ID NO:3); downstream: 5'-TCCAC-CACCCTGTTGCTGTA-3' (SEQ ID NO:4). The thermal cycling condition for PCR was 94° C. for 30 s, 60° C. for 30 s, and 72° C. for 1 min. The cycling reactions were repeated for 24 more cycles.

Quantitative RT-PCR was performed according to the manufacturer's instructions by using Applied Biosystems TaqMan® Universal Master Mix. The TNF-α TaqMan probes was purchased from the Applied Biosystems, and 18s RNA was used as an internal control. Samples were allowed to run in triplicates in each Quantitative RT-PCR assay.

Enzyme-Linked ImmunoSorbent Assay (ELISA)

Culture supernatants of the LPS-treated PBMac, with or without B22EES1-8-3 pretreatment, were collected at different time intervals and stored at −70° C. The levels of the secreted TNF-α were measured by ELISA kits specific for the cytokine (R&D system, Minneapolis, Minn.).

Preparation of Cellular Extracts

For the collection of whole cell lysate, PBMac were washed with cold PBS and incubated in cold lysis buffer (50 mM tris(hydroxymethyl)aminomethane-chloride (Tris-Cl) [pH7.4]; 150 mM sodium chloride (NaCl); 50 mM sodium fluoride (NaF); 10 mM β-glycerophosphate; 0.1 mM ethylenediaminetetraacetic acid (EDTA); 10% glycerol; 1% Triton X-100; 1 mM phenylmethanesulphonylfluoride (PMSF); 1 mM sodium orthovanadate; 2 μg/mL pepstatin A; 2 μg/mL aprotinin and 2 μg/mL leupeptin) for 20 min. The lysate was then centrifuged at 4° C. for 20 min. The supernatant was collected and stored at −70° C. until use.

To collect nuclear protein extracts, the treated cells were washed with PBS and resuspended in buffer A (10 mM 4-(2- hydroxyethyl)-1-piperazineethanesulfonic acid (HEPES) [pH7.9], 10 mM potassium chloride (KCl), 0.1 mM EDTA, 0.1 mM ethylene glycol tetraacetic acid (EGTA), 1 mM dithiothreitol (DTT), 0.5 mM phenylmethanesulphonylfluoride or phenylmethylsulphonyl fluoride (PMSF), 2 µg aprotinin, 1 mM sodium orthovanadate, 2 µg/mL pepstatin A, 2 µg/mL leupeptin and 50 mM NaF) for 15 min. After that, NP-40 at a final concentration of 0.625% was added and mixed vigorously for cell lysis.

The cell lysate was centrifuged and the supernatant containing cytoplasmic proteins was collected for storage at −70° C. The nuclear pellet was resuspended in buffer C (20 mM HEPES [pH 7.9], 0.4 M NaCl, 1 mM EDTA, 1 mM EGTA, 1 mM DTT and 1 mM PMSF) for 15 min on ice to complete lysis of the nuclear membrane. The nuclear lysate was then centrifuged, and the supernatant containing the nuclear protein was collected and stored at −70° C.[34,35].

Western Blot Analysis

Whole cell lysate (20 µg) or nuclear protein (2 µg) were separated by sodium dodecyl sulfate polyacrylamide gel electrophoresis (SDS-PAGE) and transferred to nitrocellulose membranes for probing overnight with the respective antibodies specific for the phosphorylated or total form of ERK1/2 and p38 MAPK (Cell Signaling Technology, Beverly, Mass.), NF-κB p65 protein and lamin B (Santa Cruz Biotechnology, Santa Cruz, Calif.). The membranes were incubated with the corresponding secondary antibodies conjugated with horseradish peroxidase (BD Transduction Lab, San Diego, Calif.). The signal was visualized by using enhanced chemiluminescence kit (Amersham Pharmacia Biotech). In order to quantify the results from the Western blots, the gels were scanned and the intensity of the bands was analyzed by a computer program Quantity One from BioRad.

The scope of the invention is not limited by the specific examples and suggested procedures and uses related herein since modifications can be made within such scope from the information provided by this specification to those skilled in the art.

A more complete understanding of the invention can be obtained by reference to the following specific examples of compounds, compositions, and methods of the invention. The following examples illustrate procedures for practicing the invention. These examples should not be construed as limiting. It will be apparent to those skilled in the art that the examples involve use of materials and reagents that are commercially available from known sources, e.g., chemical supply houses, so no details are given respecting them.

EXAMPLE 1

Extraction and Identification of B22EES1-8-3

A light brown powder was obtained by repeated partitioning of the EtOAc fraction prepared from the rhizomes of *Cimicifuga racemosa* and sequential chromatography on silica gel and reversed-phase HPLC. The detailed procedures are summarized in FIG. 1.

Figure 2A:
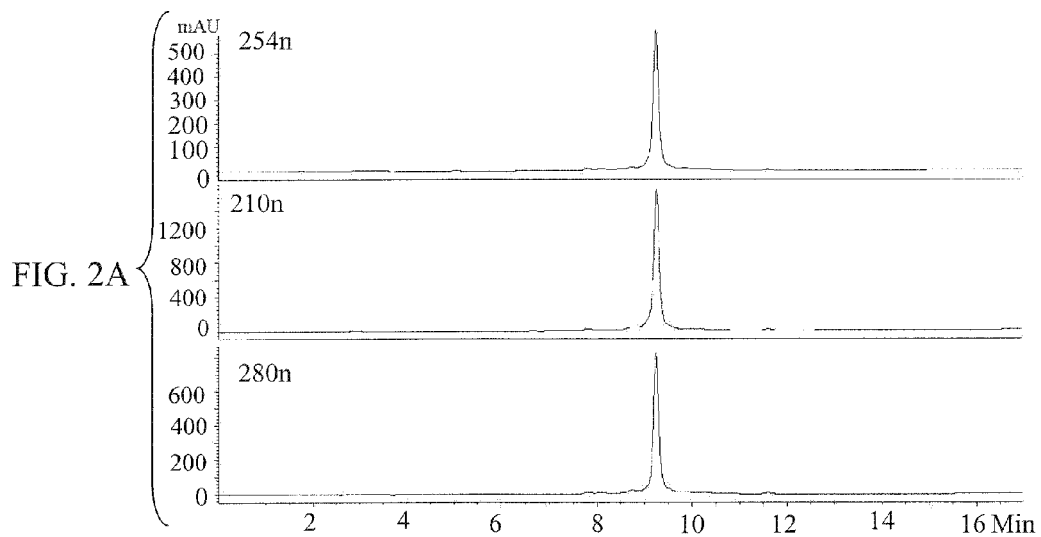
FIGS. 2A-2B show HPLC chromatogram and UV absorbance of B22EES1-8-3. The compound was purified by reversed-phase HPLC using gradient elution from 25% to 90% of acetonitrile at a flow rate of 1 mL min$^{-1}$. (A) A single peak was detected using Photo-diode Array detector at 254, 210 and 280 nm. B22EES1-8-3 was eluted at approximate 9.4 min. (B) The UV absorbance of B22EES1-8-3 maximized at 290 and 325 nm which revealed that it had a conjugated aromatic system.
Figure 2B:
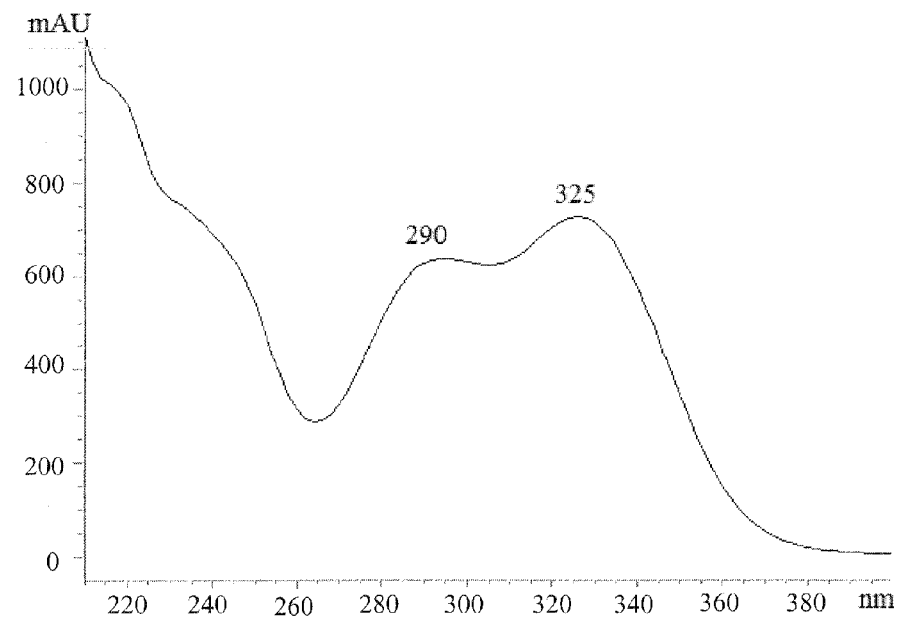
Figure 3:
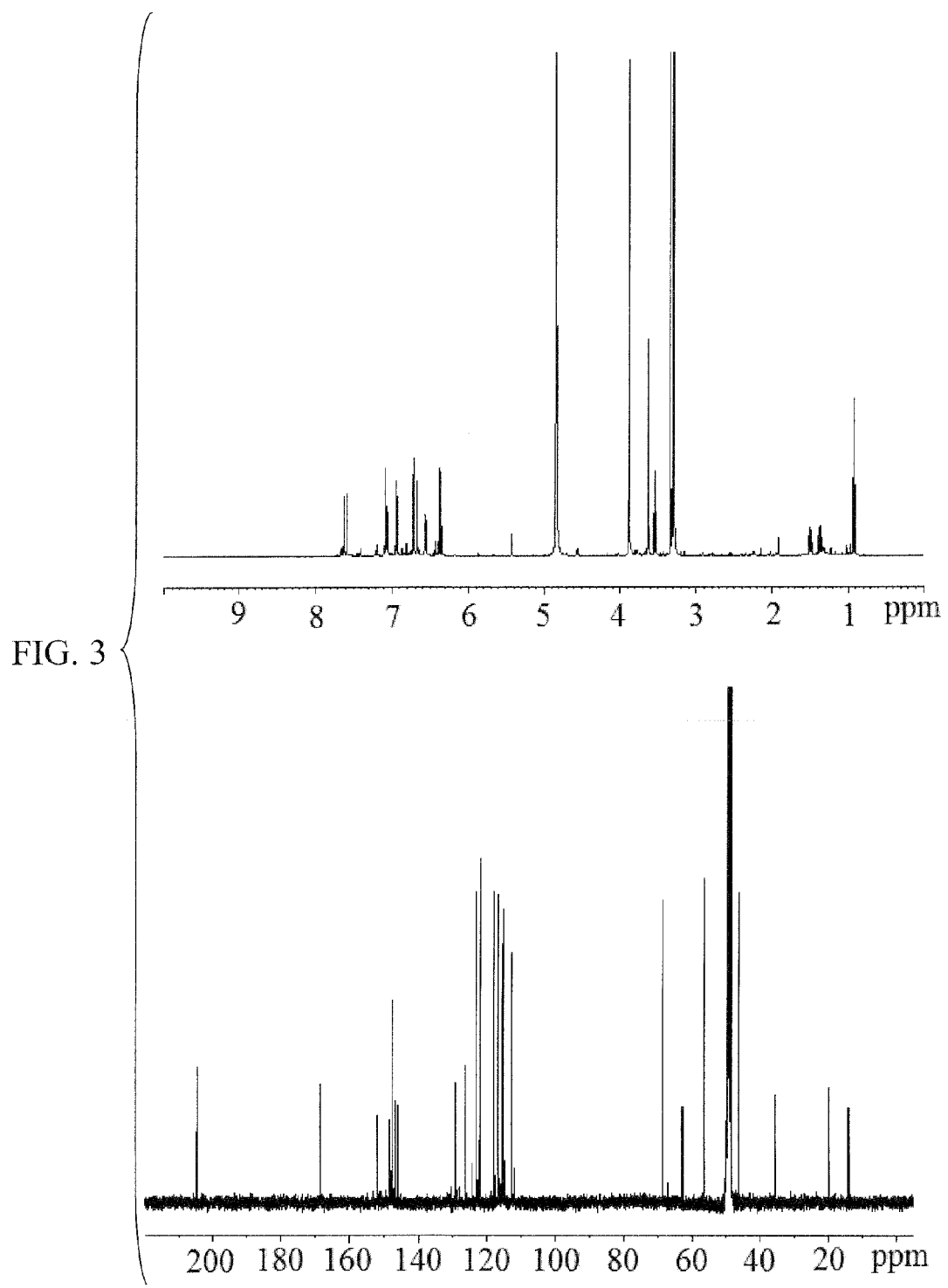
FIG. 3 shows the $^1$H (upper panel) and $^{13}$C NMR (lower panel) spectra of B22EES1-8-3. The structure of B22EES1-8-3 was elucidated by a Bruker 500 MHz DRX NMR spectrometer, operating at 500 MHz for $^1$H and at 125.765 MHz for $^{13}$C NMR, using methanol-d as the solvent.

Using HPLC, the compound was eluted at approximate 9.4 min as a single compound with UV absorbance at wavelength 254, 210 and 280 nm (FIG. 2A). In FIG. 2B, the UV absorbance of the compound maximized at 290 and 325 nm, which revealed that it has a conjugated aromatic system. The compound showed a [M]− ion peak at m/z 357.0952 in its HR-ESI-MS. Together with the $^1$H and $^{13}$C spectra data (FIG. 3), it was elucidated as B22EES1-8-3.

EXAMPLE 2

Bio-Assays

The chemical compound in *Cimicifuga racemosa* responsible for the inhibition of LPS-induced expression of TNF-α was identified. LPS is well known to be a potent inducer of TNF-α and its effects cannot be easily suppressed without the use of cytotoxic agents.

Bacterial endotoxin (lipopolysaccharide, LPS) stimulation of TNF-α induction in primary macrophages was used as a model of inflammatory diseases, since the production of TNF-α is an indicator of a key immune response.

Figure 4A:
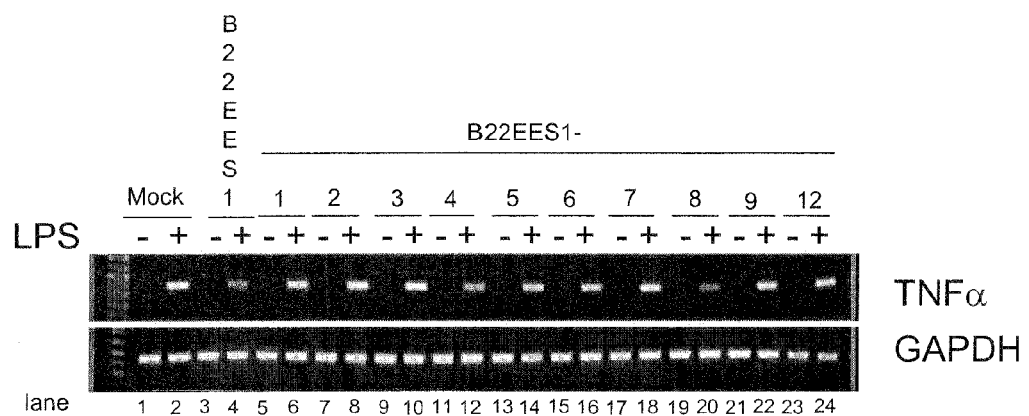
FIGS. 4A-4B show a bioassay guided fractionation of *Cimicifuga racemosa*. Primary blood macrophages (PBMac) were treated with different *C. racemosa* fractions at 100 μg/mL for 24 hr prior to the addition of 20 ng/mL LPS for 3 hr. RT-PCR (A) and quantitative RT-PCR (B) assays of TNF-α and GAPDH were performed afterwards. The results shown are representative of at least three independent experiments, with cells obtained from different donors. *P<0.05, compared with the corresponding control.
Figure 4B:
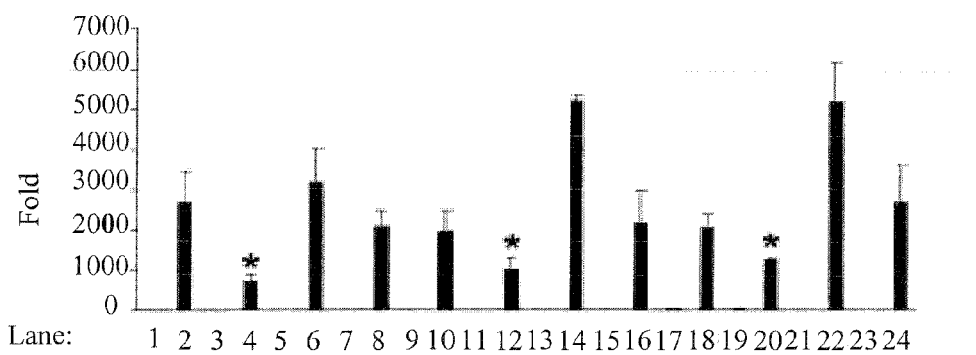

Individual extracts isolated from *Cimicifuga racemosa* were incubated with PBMac for 24 hr prior to the addition of LPS for another 3 hr. Total RNA of the treated samples was isolated and subjected to RT-PCR assays using specific human TNF-α primers. The results showed that the fraction B22EES1 inhibits LPS-induced TNF-α mRNA expression (FIG. 4A, lanes 2 and 4). Among the sub-fractions of B22EES1, only B22EES1-4 and B22EES1-8 retained the suppressive activities for TNF-α induction (FIG. 4A, lanes 12 and 20).

EXAMPLE 3

Effects of B22EES1-8-3 on LPS-Induced cytokine Production

After the identification of B22EES1-8 as being responsible for the inhibitory effects on TNF-α, the activities of B22EES1-8 sub-fractions as described above were separated and analyzed. A single molecule, namely B22EES1-8-3 (abbreviated as B8-3), was found to be the active compound in the herbal extract responsible for the anti-inflammatory effects.

To confirm the activities of B8-3 in suppressing TNF-α production, B8-3 was incubated with PBMac for 24 hr prior the addition of LPS at concentrations of 1 ng/mL and 10 ng/mL for 24 hr. The culture supernatants were collected and measured by ELISA for the level of secreted TNF-α.

Figure 5A:
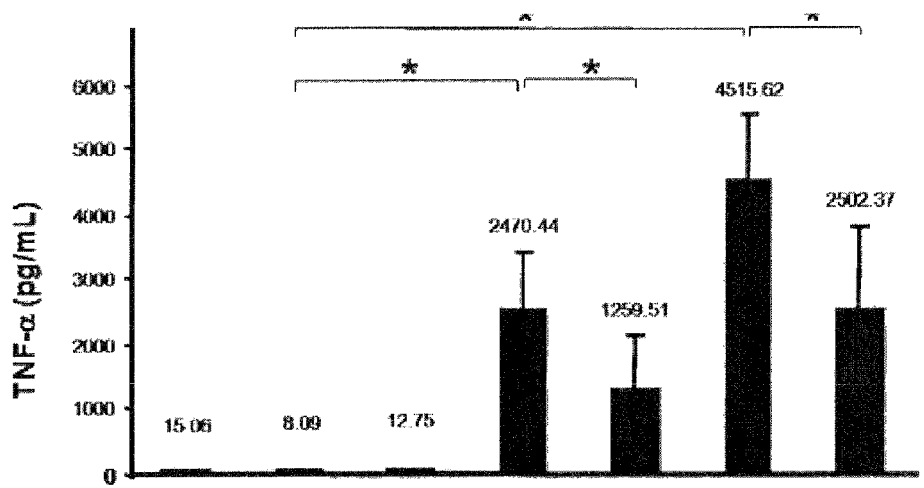
FIGS. 5A-5B show inhibition of LPS-induced TNF-α production by B22EES1-8-3 and dexamethasone. PBMac were incubated with (A) 140 μM B22EES1-8-3 or (B) 1.3 or 5.1 μM dexamethasone (Dex) for 24 hr prior to the addition of 1 ng/mL and 10 ng/mL LPS for another 24 hr. The culture supernatants were collected and assayed for TNF-α by ELISA. The results shown were the mean values±standard derivation (S.D.) of 6 independent experiments, with cells obtained from different donors. *P<0.05, compared with the corresponding control.
Figure 5B:
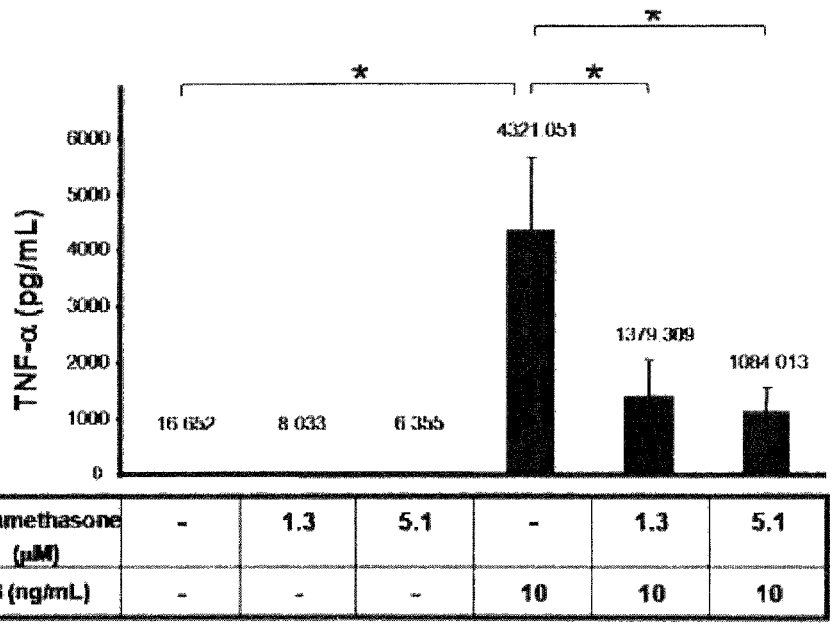

B8-3 inhibited the LPS-induced TNF-α protein production by 47±19% and 58±30% at LPS concentrations of 1 ng/mL and 10 ng/mL, respectively (FIG. 5A, lanes 4 vs 5 and lanes 6 vs 7).

To further compare the efficiency of B8-3 with existing drugs, dexamethasone, a potent immunosuppressive corticosteroid, was used as a prototype. PBMac were treated with dexamethasone for 24 hr prior to the addition of LPS at concentrations of 1 ng/mL and 10 ng/mL for 24 hr.

The results demonstrate that dexamethasone causes a significant inhibition of LPS-induced TNF-α production by 32±7.5% and 25±6.3% at concentrations of 1.3 and 5.1 µM, respectively (FIG. 5B).

EXAMPLE 4

Molecular Mechanisms of Cytokine Downregulation by B8-3

The molecular pathways involved in B8-3 inhibition of LPS-induced TNF-α production were elucidated. It is well documented that the activation of cytokine production in LPS-treated cells is initiated by the binding of LPS to its receptor[38]. After binding to the receptor, a cascade of signaling kinases is activated. Among the activated kinases, MAP kinases play a crucial role in LPS-induced cytokine production. Previous studies illustrated that the induction of TNF-α by LPS and other pathogens requires the phosphorylation and activation of ERK1/2 and p38 MAPK[13,14,39].

In order to study the role of MAP kinases in B8-3 inhibition of TNF-α production, PBMac were treated with B8-3 for 24 hr and followed by the addition of LPS for 15 min. Protein samples were collected afterward and Western blots were performed.

The results showed that LPS treatment results in phosphorylation of two different MAP kinases, namely ERK1/2 and p38 MAPK (FIG. 6. lane 2). With B8-3 pretreatment, the phosphorylation of ERK1/2 (FIG. 6A, lanes 2 vs 4) but not p38 MAPK induced by LPS was suppressed (FIG. 6B, lanes 2 vs 4).

These results demonstrated that the anti-inflammatory activity of B8-3 may be in part due to its inhibition of ERK1/2 phosphorylation.

Along the signaling pathways regulated by MAP kinases in response to LPS treatment, activation of the transcription factor NF-κB plays a critical role in the induction of proinflammatory cytokines including TNF-α[40]. The activation of NF-κB involves degradation of its specific inhibitor IκB and translocation of NF-κB sub-units from the cytoplasm to the nucleus. In accordance with the subject invention, the addition of B8-3 for 24 hr prior the addition of LPS reduced the translocation of NF-κB p65 subunit into the nucleus.

The results showed that the addition of B8-3 to PBMac for 24 hr prior to the addition of LPS reduced the amount of p65NF-kB in the nuclear fraction (FIG. 6C, lanes 2 vs 4), indicating that the translocation of the p65NF-kB to the nucleus was inhibited by B8-3. In general, B8-3 can inhibit LPS-induced kinase activities and their consequent activation of the nuclear transcription factor for TNF-α transcription. Thus, the compounds of the subject invention can be used to regulate intracellular and/or extracellular activities that are downstream from NF-kB and/or ERK1/2 in the cascade of cellular events associated with inflammatory conditions.

EXAMPLE 5

Figures 7A, 7B:
FIGS. 7A-7B show the HPLC chromatograms of CF22EES1-8 (A) and CH22EES1-8 (B). Herbs *C. foetida* and *C. heracleifolia* were extracted following the extraction procedure of *C. racemosa*. Their extracts (CF22EES1-8 and CH22EES1-8) were injected into the HPLC using the same condition as that of B22EES1-8-3 and the chromatograms were recorded. The chromatograms showed the presence of a compound (with *) with retention time at approximate 9.4 minutes.

Determination the Presence of B22EES1-8-3 in *Cimicifuga foetida* and *Cimicifuga heracleifolia* Using HPLC-UV Under the same HPLC conditions, the retention time and the UV absorbance of B8-3 were compared with the characteristic peak in the chromatograms of CF22EES1 and CH22EES1-8. In FIGS. 7A and B, both samples had a peak with retention time at approximate 9.4 min and their respective UV absorbance was same as that of B8-3 (FIGS. 2A & B). The results revealed that herbs including *C. foetida* and *C. heracleifolia* contained B8-3.

EXAMPLE 6

Figure 8A:
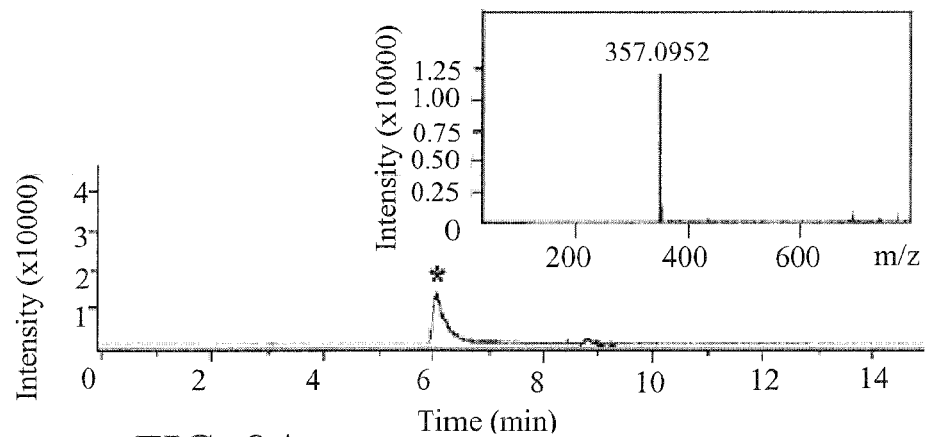
FIGS. 8A-8C show the HPLC chromatograms and HRESI-MS spectra of (A) B22EES1-8-3, (B) CH22EES1-8, and (C) CH22EES1-8. Herbs *C. foetida* and *C. heracleifolia* were extracted following the extraction procedure of *C. racemosa*. Their fractions (CH22EES1-8 and CH22EES1-8) were injected into an HPLC-coupled high-resolution ESI-TOF-MS using the same condition as that of B22EES1-8-3. The chromatograms showed the presence of a compound (with *) with retention time at approximately 6 min and with an ion peak at 357 m/z.
Figure 8B:
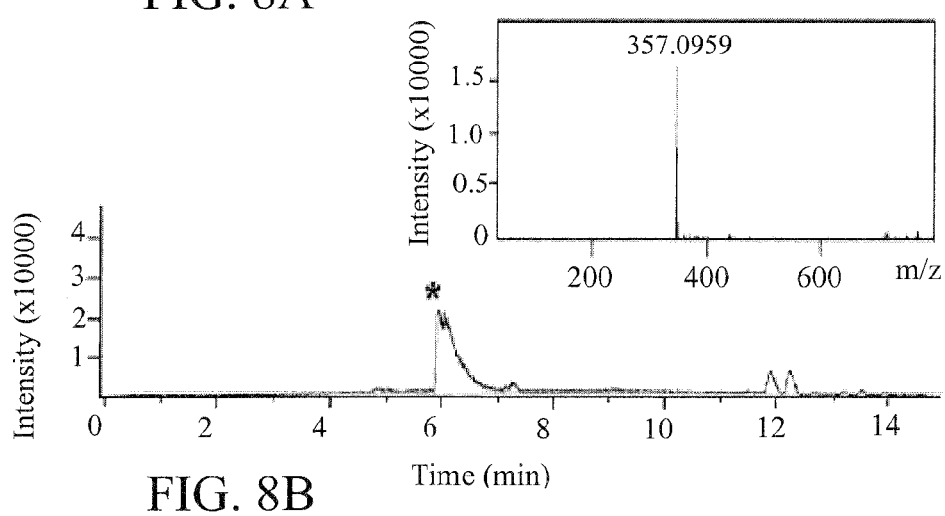
Figure 8C:
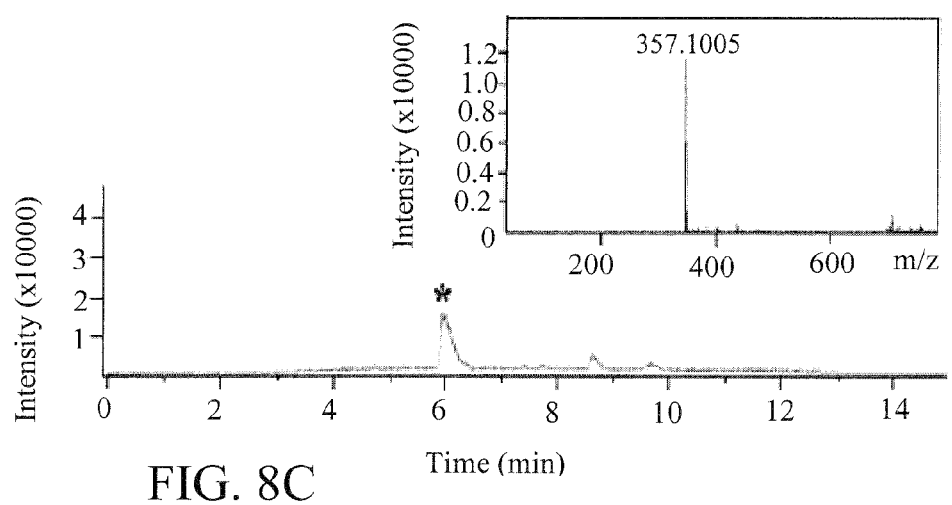

Determination the Presence of B22EES1-8-3 in *Cimicifuga foetida* and *Cimicifuga heracleifolia* Using HPLC-TOF-MS Under the same HPLC and ESI-MS conditions, the retention time and the mass-to-charge ratio of B8-3 were compared to the characteristic peak in the chromatograms and spectra of CF22EES1-8 and CH22EES1-8. In FIGS. 8B and C, both samples had a peak with retention time at approximate 6 min with an ion peak at m/z 357 that was the same as that of compound 1 (FIG. 8A). The results revealed that herbs including *C. foetida* and *C. heracleifolia* contained B8-3.

REFERENCES

1. Aggarwal B B, Shishodia S, Sandur S K, Pandey M K, Sethi G. Inflammation and cancer: how hot is the link? Biochem Pharmacol. 2006; 72:1605-1621.
2. Woodworth C D, McMullin E, Iglesias M, Plowman G D. Interleukin 1 alpha and tumor necrosis factor alpha stimulate autocrine amphiregulin expression and proliferation of human papillomavirus-immortalized and carcinoma-derived cervical epithelial cells. Proc Natl Acad Sci USA. 1995; 92:2840-2844.
3. Montesano R, Soulie P, Eble J A, Carrozzino F. Tumour necrosis factor alpha confers an invasive, transformed phenotype on mammary epithelial cells. J Cell Sci. 2005; 118:3487-3500.
4. Cheng S M, Xing B, Li J C, Cheung B K, Lau A S. Interferon-gamma regulation of TNFalpha-induced matrix metalloproteinase 3 expression and migration of human glioma T98G cells. Int J Cancer. 2007; 121:1190-1196.
5. van der Poll T, Opal S M. Host-pathogen interactions in sepsis. Lancet Infect Dis. 2008; 8:32-43.
6. Raetz C R. Biochemistry of endotoxins. Annu Rev Biochem. 1990; 59:129-170.
7. Bone R C. Gram-negative sepsis. Background, clinical features, and intervention. Chest. 1991; 100:802-808.
8. Raetz C R, Ulevitch R J, Wright S D, Sibley C H, Ding A, Nathan C F. Gram-negative endotoxin: an extraordinary lipid with profound effects on eukaryotic signal transduction. Faseb J. 1991; 5:2652-2660.
9. Tracey K J, Cerami A. Tumor necrosis factor: a pleiotropic cytokine and therapeutic target. Annu Rev Med. 1994; 45:491-503.
10. Shakhov A N, Collart M A, Vassalli P, Nedospasov S A, Jongeneel C V. Kappa B-type enhancers are involved in lipopolysaccharide-mediated transcriptional activation of the tumor necrosis factor alpha gene in primary macrophages. J Exp Med. 1990; 171:35-47.
11. Ziegler-Heitbrock H W, Sternsdorf T, Liese J, et al. Pyrrolidine dithiocarbamate inhibits NF-kappa B mobilization and TNF production in human monocytes. J Immunol. 1993; 151:6986-6993.
12. Trede N S, Tsytsykova A V, Chatila T, Goldfeld A E, Geha R S. Transcriptional activation of the human TNF-alpha promoter by superantigen in human monocytic cells: role of NF-kappa B. J Immunol. 1995; 155:902-908.
13. Cheung B K, Lee D C, Li J C, Lau Y L, Lau A S. A role for double-stranded RNA-activated protein kinase PKR in *Mycobacterium*-induced cytokine expression. J Immunol. 2005; 175:7218-7225.
14. Li J C, Lee D C, Cheung B K, Lau A S. Mechanisms for HIV Tat upregulation of IL-10 and other cytokine expression: kinase signaling and PKR-mediated immune response. FEBS Lett. 2005; 579:3055-3062.
15. Lee D C, Cheung C Y, Law A H, Mok C K, Peiris M, Lau A S. p38 mitogen-activated protein kinase-dependent hyperinduction of tumor necrosis factor alpha expression in response to avian influenza virus H5N1. J. Virol. 2005; 79:10147-10154.
16. Davis R J. The mitogen-activated protein kinase signal transduction pathway. J Biol Chem. 1993; 268:14553-14556.

17. Su B, Karin M. Mitogen-activated protein kinase cascades and regulation of gene expression. Curr Opin Immunol. 1996; 8:402-411.
18. Chan-Hui P Y, Weaver R. Human mitogen-activated protein kinase kinase kinase mediates the stress-induced activation of mitogen-activated protein kinase cascades. Biochem J. 1998; 336 (Pt 3):599-609.
19. Herlaar E, Brown Z. p38 MAPK signalling cascades in inflammatory disease. Mol Med Today. 1999; 5:439-447.
20. Ichijo H. From receptors to stress-activated MAP kinases. Oncogene. 1999; 18:6087-6093.
21. Pando M P, Verma I M. Signal-dependent and -independent degradation of free and NF-kappa B-bound Ikappa-Balpha. J Biol Chem. 2000; 275:21278-21286.
22. Abate A, Oberle S, Schroder H. Lipopolysaccharide-induced expression of cyclooxygenase-2 in mouse macrophages is inhibited by chloromethylketones and a direct inhibitor of NF-kappa B translocation. Prostaglandins Other Lipid Mediat. 1998; 56:277-290.
23. Chen F, Castranova V, Shi X, Demers L M. New insights into the role of nuclear factor-kappaB, a ubiquitous transcription factor in the initiation of diseases. Clin Chem. 1999; 45:7-17.
24. Grabley S, Thiericke R. Bioactive agents from natural sources: trends in discovery and application. Adv Biochem Eng Biotechnol. 1999; 64:101-154.
25. Habtemariam S. Natural inhibitors of tumour necrosis factor-alpha production, secretion and function. Planta Med. 2000; 66:303-313.
26. Blumenthal M GAaBJ. Herbal Medicine: Expanded Commission E Monographs. Newton, Mass.: Integrative Medicine Communications. 2000:22-27.
27. Boon H S M. The Pharmacology of 47 Common Herbs. Kingston, Ontario, Canada: Quarry Health Books; 1999.
28. Kronenberg F, Fugh-Berman A. Complementary and alternative medicine for menopausal symptoms: a review of randomized, controlled trials. Ann Intern Med. 2002; 137:805-813.
29. Sakurai N, Nagai M. [Chemical constituents of original plants of *Cimicifugae rhizoma* in Chinese medicine]. Yakugaku Zasshi. 1996; 116:850-865.
30. Sakai S, Kawamata H, Kogure T, et al. Inhibitory effect of ferulic acid and isoferulic acid on the production of macrophage inflammatory protein-2 in response to respiratory syncytial virus infection in RAW264.7 cells. Mediators Inflamm. 1999; 8:173-175.
31. Kim S J, Kim M S. Inhibitory effects of *cimicifugae rhizoma* extracts on histamine, bradykinin and COX-2 mediated inflammatory actions. Phytother Res. 2000; 14:596-600.
32. Burdette J E, Chen S N, Lu Z Z, et al. Black cohosh (*Cimicifuga racemosa* L.) protects against menadione-induced DNA damage through scavenging of reactive oxygen species: bioassay-directed isolation and characterization of active principles. J Agric Food Chem. 2002; 50:7022-7028.
33. Tian Z, Pan R, Chang Q, Si J, Xiao P, Wu E. *Cimicifuga foetida* extract inhibits proliferation of hepatocellular cells via induction of cell cycle arrest and apoptosis. J Ethnopharmacol. 2007; 114:227-233.
34. Cheung B K, Lee D C, Li J C, Lau Y L, Lau A S. A Role for Double-Stranded RNA-Activated Protein Kinase PKR in *Mycobacterium*-Induced Cytokine Expression. J Immunol. 2005; 175:7218-7225.
35. Schreiber E, Matthias P, Muller M M, Schaffner W. Rapid detection of octamer binding proteins with 'mini-extracts', prepared from a small number of cells. Nucleic Acids Res. 1989; 17:6419.
36. Duker E M, Kopanski L, Jarry H, Wuttke W. Effects of extracts from *Cimicifuga racemosa* on gonadotropin release in menopausal women and ovariectomized rats. Planta Med. 1991; 57:420-424.
37. Qiu S X, Dan C, Ding L S, et al. A triterpene glycoside from black cohosh that inhibits osteoclastogenesis by modulating RANKL and TNFalpha signaling pathways. Chem Biol. 2007; 14:860-869.
38. Lu Y C, Yeh W C, Ohashi P S. LPS/TLR4 signal transduction pathway. Cytokine. 2008; 42:145-151.
39. Kim S H, Kim J, Sharma R P. Inhibition of p38 and ERK MAP kinases blocks endotoxin-induced nitric oxide production and differentially modulates cytokine expression. Pharmacol Res. 2004; 49:433-439.
40. Blackwell T S, Christman J W. The role of nuclear factor-kappa B in cytokine gene regulation. Am J Respir Cell Mol Biol. 1997; 17:3-9.
41. Panes J, Gomollon F, Taxonera C, Hinojosa J, Clofent J, Nos P. Crohn's disease: a review of current treatment with a focus on biologics. Drugs. 2007; 67:2511-2537.
42. Saunders B M, Britton W J. Life and death in the granuloma: immunopathology of tuberculosis. Immunol Cell Biol. 2007; 85:103-111.
43. Clay H, Volkman H E, Ramakrishnan L. Tumor necrosis factor signaling mediates resistance to mycobacteria by inhibiting bacterial growth and macrophage death. Immunity. 2008; 29:283-294.
44. Ohlsson K, Bjork P, Bergenfeldt M, Hageman R, Thompson R C. Interleukin-1 receptor antagonist reduces mortality from endotoxin shock. Nature. 1990; 348:550-552.
45. Tracey K J, Fong Y, Hesse D G, et al. Anti-cachectin/TNF monoclonal antibodies prevent septic shock during lethal bacteraemia. Nature. 1987; 330:662-664.
46. Schett G. Review: Immune cells and mediators of inflammatory arthritis. Autoimmunity. 2008; 41:224-229.

We claim:

1. A method for treating arthritis, wherein said method comprises administering, to a subject in need of such treatment, an effective amount of an isolated compound or a salt thereof, wherein said compound has the following formula:

[Chemical structure]

wherein
- $R_1$ is alkyl;
- $R_2$ is H or alkyl;
- $R_3$, $R_4$, and $R_5$ are independently —H, acyl, halo, haloalkyl, amino, alkylamino, hydroxyl, alkyl, hydroxylalkyl, or —COOH;
- $R_6$ is —O or —NH;
- $R_7$ is —H, alkyl, alkoxy, hydroxylalkyl, hydroxyl, or halo;
- $R_8$, $R_9$, and $R_{12}$ are independently —H, acyl, halo, amino, alkylamino, hydroxyl, alkyl, hydroxylalkyl, or —COOH;
- $R_{10}$ is H or alkyl; and
- $R_{11}$ is H or alkyl.

2. The method, according to claim 1, wherein the subject is a human.

3. The method, according to claim 1, wherein the $R_2$ is H, $R_3$ is H, and $R_4$ is H.

4. The method, according to claim 3, wherein $R_1$ is a methyl group.

5. The method, according to claim 1, wherein TNF-α activity is inhibited.

6. The method, according to claim 1, used to rheumatoid arthritis.

7. The method, according to claim 1, wherein the subject is a mammal.

8. The method, according to claim 7, wherein the mammal is cattle.

9. The method, according to claim 1, wherein ERK1/2 phosphorylation is inhibited.

10. The method, according to claim 1, wherein said compound is:

[Chemical structure]

11. The method, according to claim 1, wherein NF-kB activation is suppressed.

* * * * *

UNITED STATES PATENT AND TRADEMARK OFFICE
CERTIFICATE OF CORRECTION

PATENT NO. : 8,377,987 B2
APPLICATION NO. : 12/647843
DATED : February 19, 2013
INVENTOR(S) : Allan Sik Yin Lau et al.

Page 1 of 1

It is certified that error appears in the above-identified patent and that said Letters Patent is hereby corrected as shown below:

In the Specifications:

Column 5,
Line 59, "(B) CH22EES1-8" should read --(B) CF22EES1-8F--.
Line 62, "(CH22EES1-8" should read --(CF22EES1-8--.

In the Claims:

Column 22,
Line 40, "used to rheumatoid" should read --used to treat rheumatoid--.

Signed and Sealed this
Sixth Day of August, 2013

Teresa Stanek Rea
*Acting Director of the United States Patent and Trademark Office*

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: PCR Primer set for TNF-alpha (upstream)

<400> SEQUENCE: 1
ggctccaggc ggtgcttgtc c                                             21
```

```
<210> SEQ ID NO 2
<211> LENGTH: 20
<212> TYPE: DNA
<213> ORGANISM: Artificial Sequence
<220> FEATURE:
<223> OTHER INFORMATION: PCR Primer set for TNF-alpha (downstream)

<400> SEQUENCE: 2
agacggcgat gcggctgatg                                                   20

<210> SEQ ID NO 3
<211> LENGTH: 20
<212> TYPE: DNA
<213> ORGANISM: Artificial Sequence
<220> FEATURE:
<223> OTHER INFORMATION: PCR Primer set for GAPDH (upstream)

<400> SEQUENCE: 3
accacagtcc atgccatcac                                                   20

<210> SEQ ID NO 4
<211> LENGTH: 20
<212> TYPE: DNA
<213> ORGANISM: Artificial Sequence
<220> FEATURE:
<223> OTHER INFORMATION: PCR Primer set for GAPDH (downstream)

<400> SEQUENCE: 4
tccaccaccc tgttgctgta                                                   20
```